(12) United States Patent
Miyazaki

(10) Patent No.: US 7,363,658 B2
(45) Date of Patent: Apr. 22, 2008

(54) PERSONAL INFORMATION INTERMEDIARY METHOD

(75) Inventor: Tatsuya Miyazaki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 462 days.

(21) Appl. No.: 09/956,091

(22) Filed: Sep. 20, 2001

(65) Prior Publication Data
US 2002/0188851 A1 Dec. 12, 2002

(30) Foreign Application Priority Data
Jun. 6, 2001 (JP) ............................. 2001-170455

(51) Int. Cl.
*G06F 17/30* (2006.01)
*G06F 7/00* (2006.01)
*G06Q 50/00* (2006.01)

(52) U.S. Cl. ............................. 726/26; 707/10; 705/2
(58) Field of Classification Search ................ 713/200; 726/26; 707/10; 705/2
See application file for complete search history.

(56) References Cited

U.S. PATENT DOCUMENTS

| | | | | |
|---|---|---|---|---|
| 5,440,541 A | * | 8/1995 | Iida et al. | 370/352 |
| 5,537,590 A | * | 7/1996 | Amado | 707/2 |
| 6,070,148 A | * | 5/2000 | Mori et al. | 705/26 |
| 6,308,203 B1 | * | 10/2001 | Itabashi et al. | 709/217 |
| 6,327,359 B1 | * | 12/2001 | Kang et al. | 379/221.08 |
| 6,505,106 B1 | * | 1/2003 | Lawrence et al. | 701/35 |
| 6,505,230 B1 | * | 1/2003 | Mohan et al. | 709/202 |
| 6,651,090 B1 | * | 11/2003 | Itabashi et al. | 709/217 |
| 6,654,891 B1 | * | 11/2003 | Borsato et al. | 713/201 |
| 6,697,836 B1 | * | 2/2004 | Kawano et al. | 709/202 |
| 2002/0065701 A1 | * | 5/2002 | Kim et al. | 705/9 |
| 2002/0138761 A1 | * | 9/2002 | Kanemaki et al. | 713/201 |

FOREIGN PATENT DOCUMENTS

WO WO 0033210 A * 6/2000

OTHER PUBLICATIONS

"WebMail for the UCI Libraries," Summer 2000, pp. 1-15.*

* cited by examiner

*Primary Examiner*—Emmanuel L. Moise
*Assistant Examiner*—Michael Pyzocha
(74) *Attorney, Agent, or Firm*—Staas & Halsey LLP

(57) ABSTRACT

In a personal information intermediary method of the invention, a first recording medium stores respective items of personal information of registered users and a second recording medium stores respective items of destination information of registered local terminals. A transmission request, including a personal information selection result and a destination selection result, which is sent by a particular user among the registered users, is received. A personal information item is read from the first recording medium, the personal information item corresponding to the personal information selection result of the transmission request. A destination information item is read from the second recording medium, the destination information item corresponding to the destination selection result of the received transmission request. The personal information item of the particular user is transmitted to a particular local terminal among the registered local terminals that is indicated by the destination information item.

5 Claims, 12 Drawing Sheets

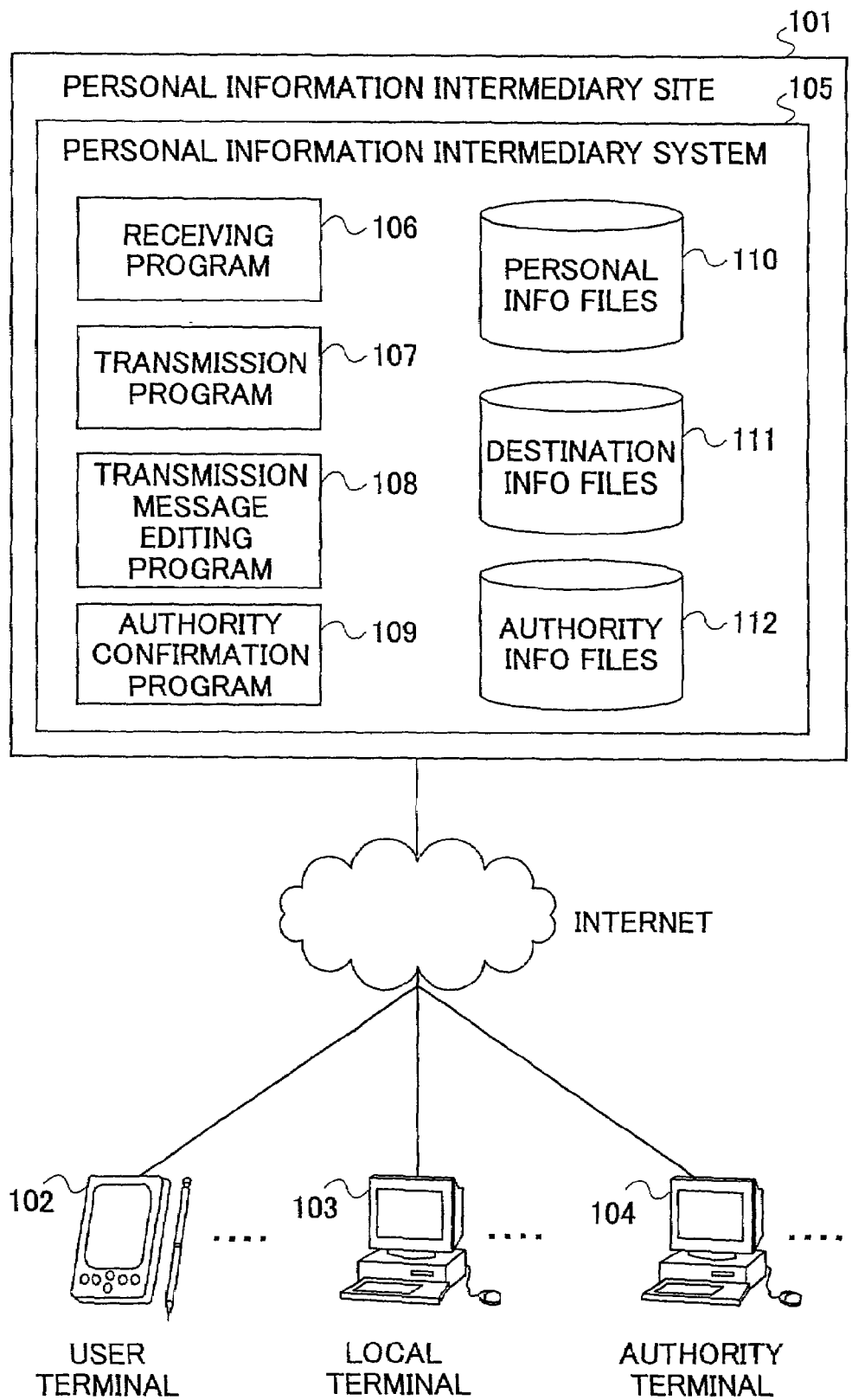

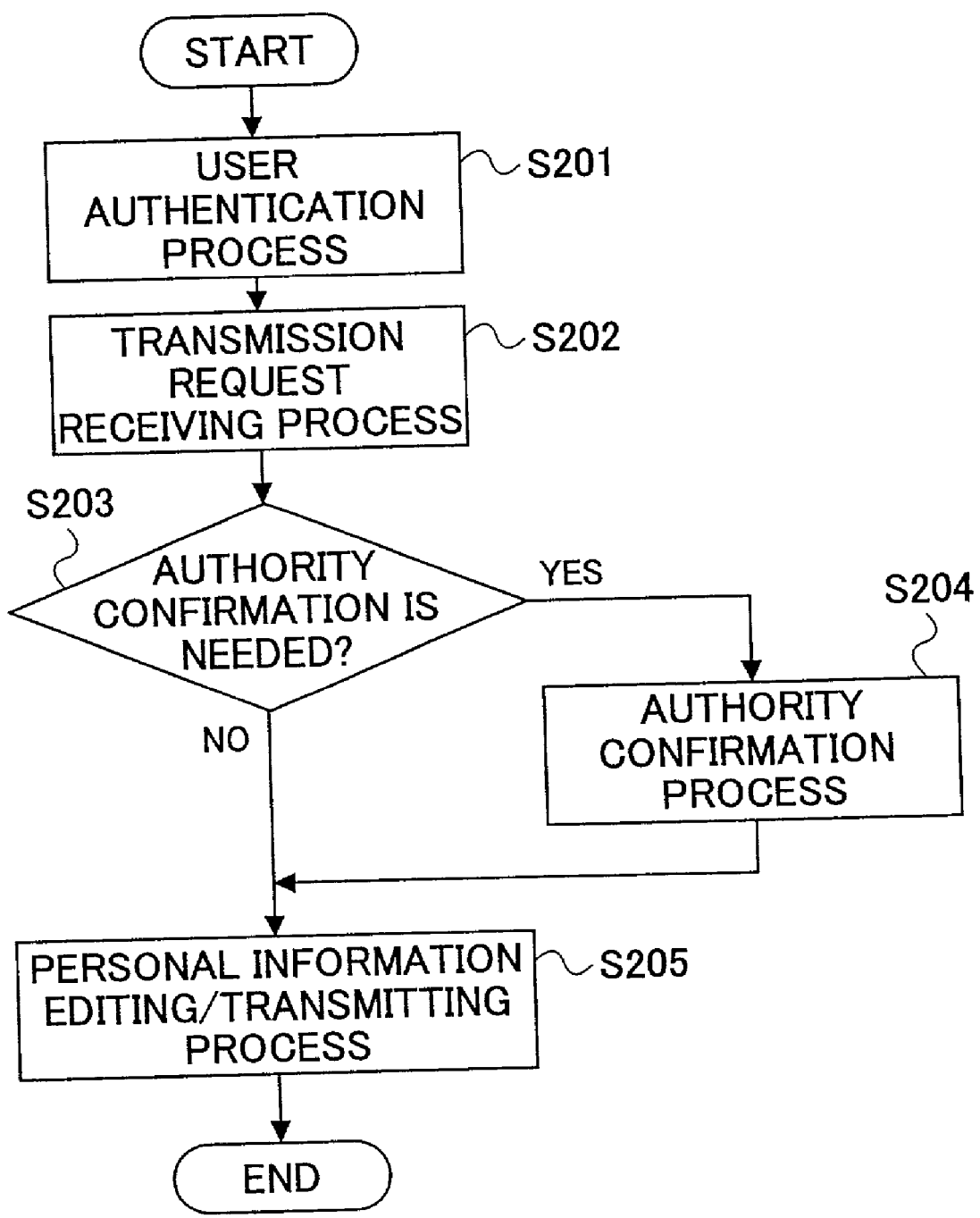

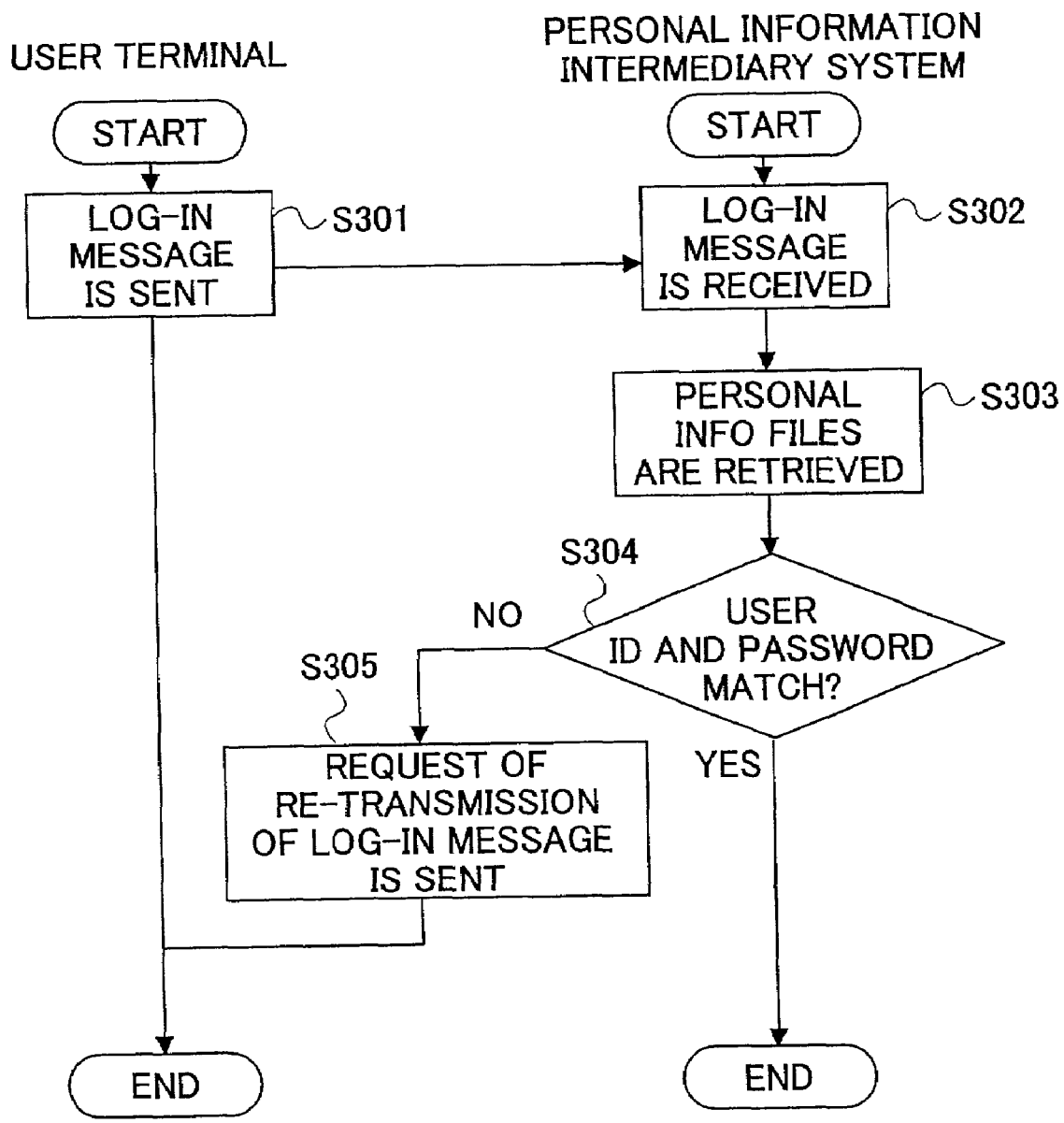

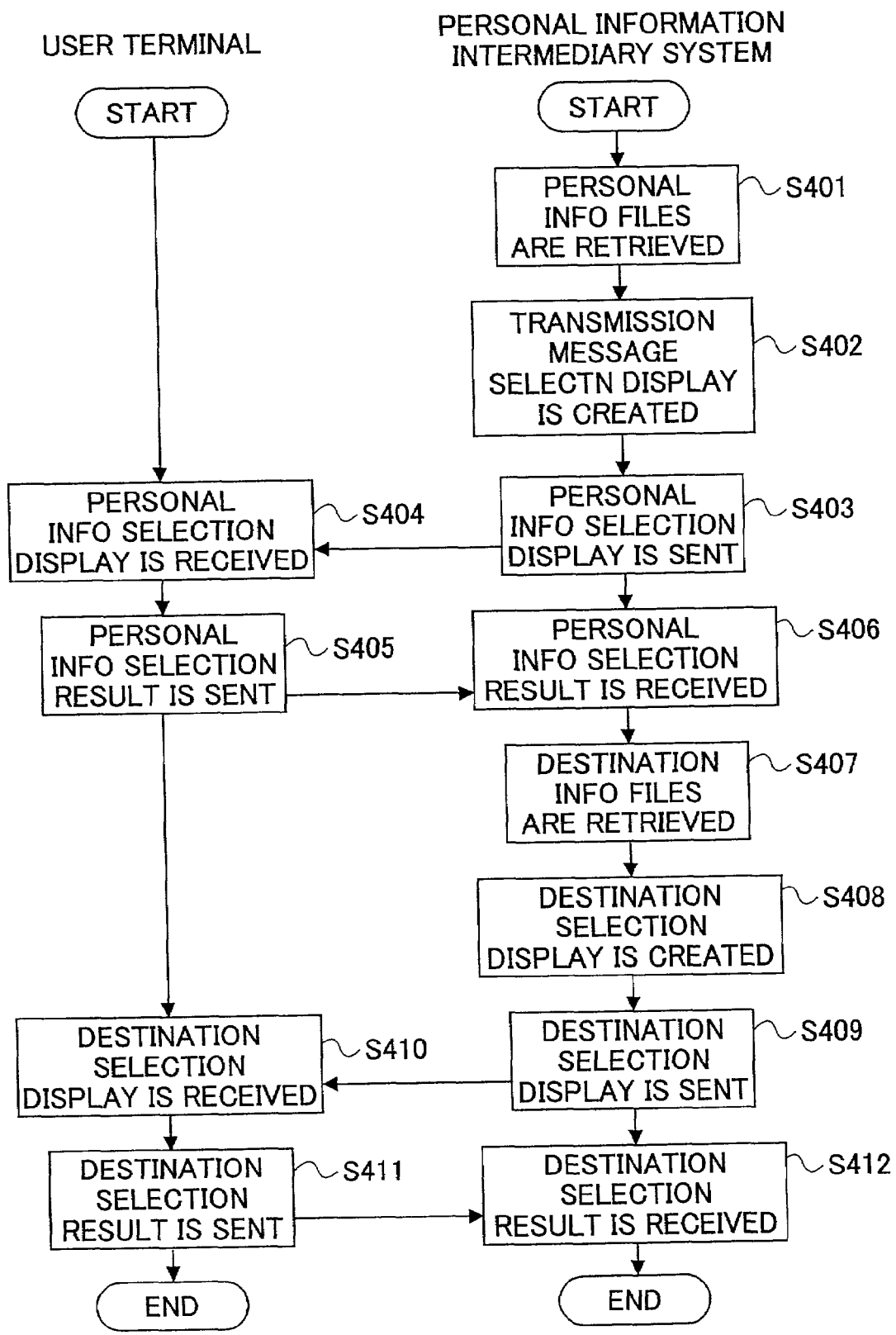

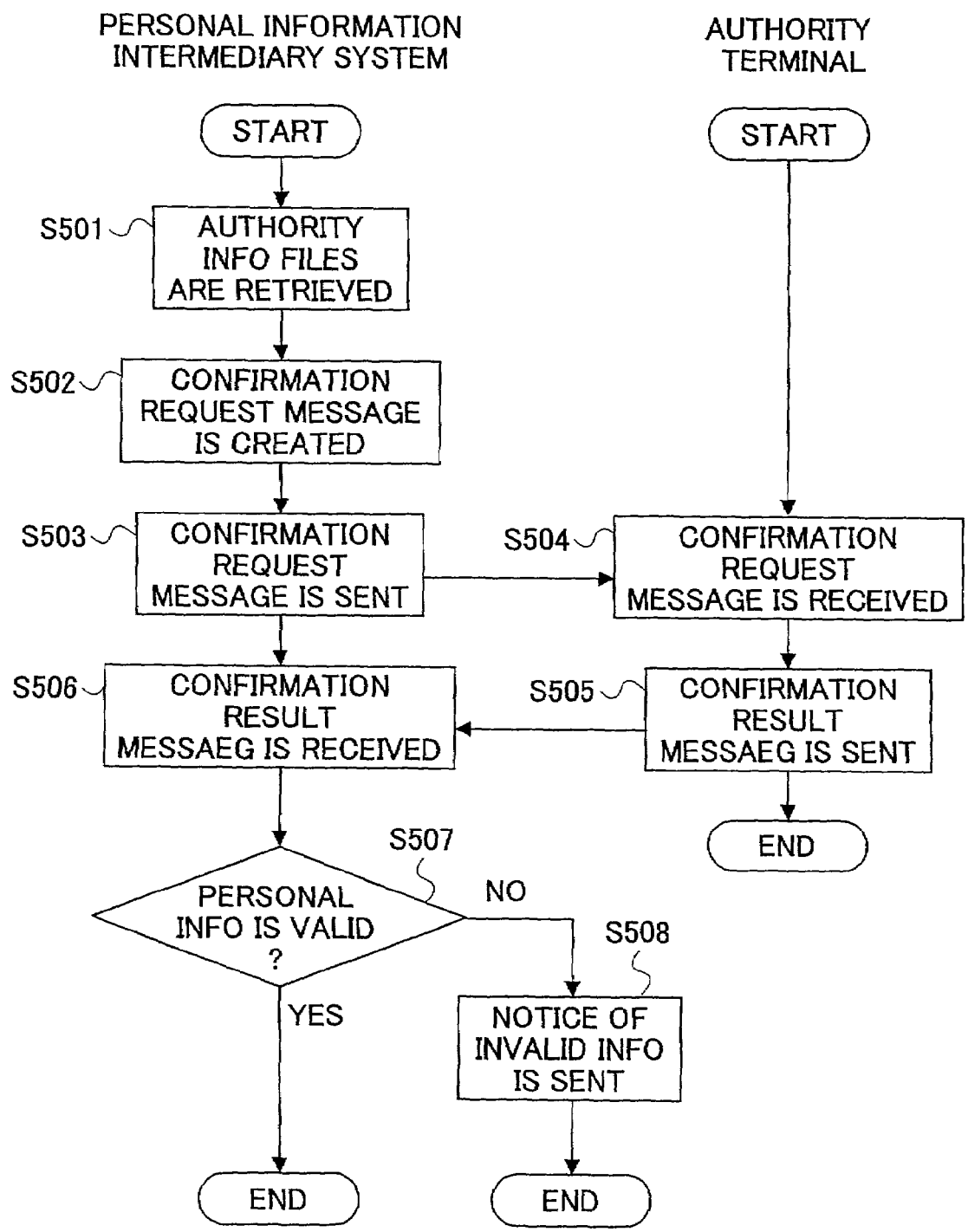

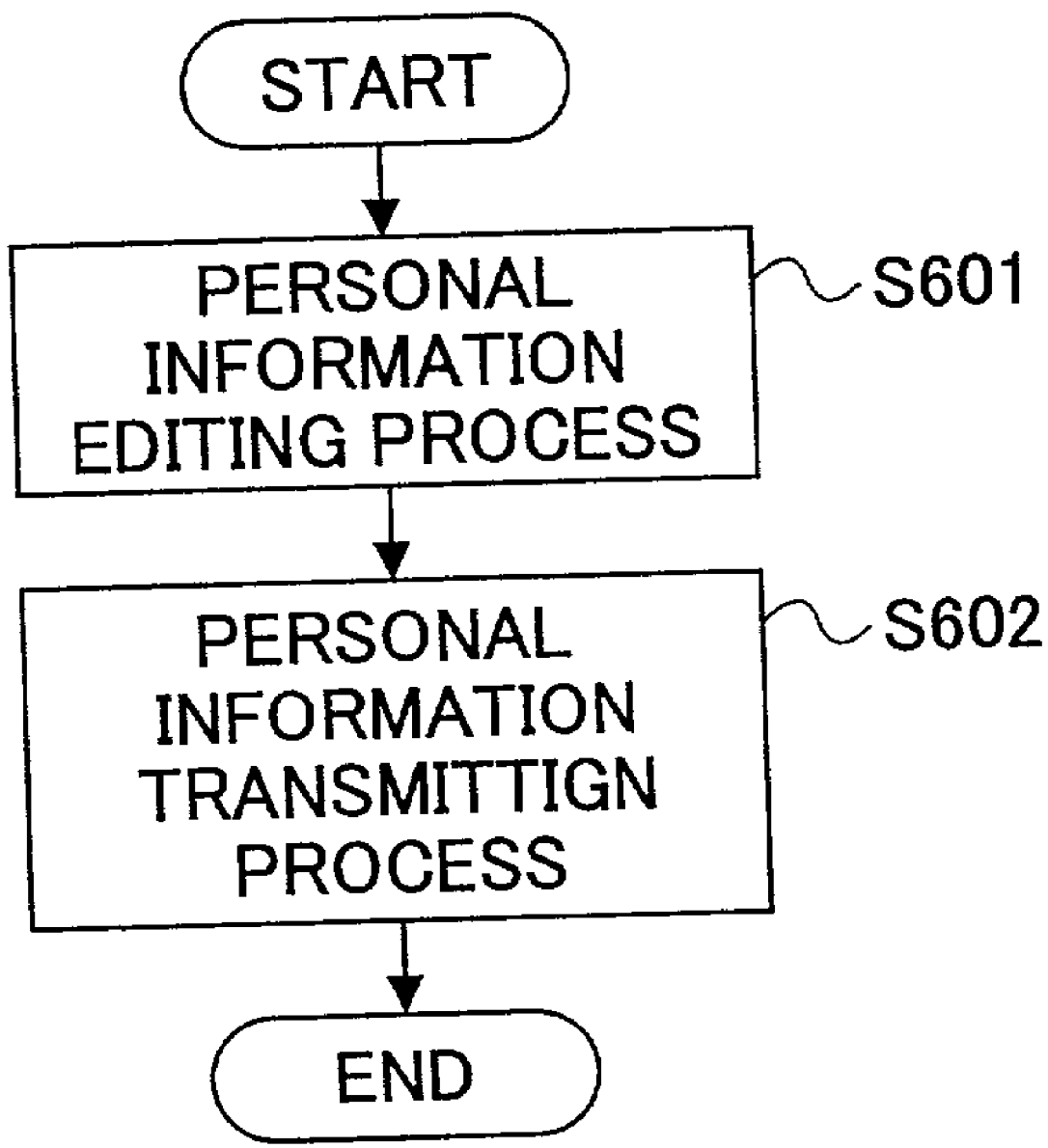

FIG.7

USER FILE

| USER ID | PASS WORD | USER NAME | ADDRESS | PHONE NO. | E-MAIL ADDRESS | HIC | DL |
|---|---|---|---|---|---|---|---|
| yamada | 123 | yamada taro | K city | 123-4567 | yamada@xxx.com | 1 | 1 |
| sato | 456 | sato hanako | Y city | 890-1234 | sato@xxx.com | 1 | 0 |
| suzuki | 789 | suzuki ken | O city | 567-8901 | suzuki@xxx.com | 0 | 0 |
| ... | | | | | | | |

701

HEALTH INSURANCE CERTIFICATE FILE

| USER ID | SYMBOL | CERTIFICATE NO. | SEX | DATE OF BIRTH | INSURANCE NO. | DATE OF ISSUANCE |
|---|---|---|---|---|---|---|
| yamada | 1111 | 111111 | 1 | 1967/10/09 | 11111111 | 2000/04/01 |
| sato | 2222 | 222222 | 2 | 1967/04/11 | 222222 | 2000/04/01 |
| suzuki | 3333 | 333333 | 1 | 1965/01/01 | 33333333 | 2000/08/01 |
| ... | | | | | | |

702

DRIVER'S LICENSE FILE

| USER ID | DATE OF BIRTH | LICENSSE NO. | IMAGE INDEX | EXPIRATION DATE |
|---|---|---|---|---|
| yamada | 1967/10/09 | 1111111111 | C:\data\license\1111111111.gif | 2001/10/09 |
| sato | 1967/04/11 | 2222222222 | C:\data\license\2222222222.gif | 2002/04/11 |
| suzuki | 1965/01/01 | 3333333333 | C:\data\license\3333333333.gif | 2002/01/01 |
| ... | | | | |

INSURANCE AUTHORITY FILE 801

| INSURANCE NO. | I/A NAME | PHONE NO. | E-MAIL ADDRESS |
|---|---|---|---|
| 11111111 | A | 111-1111 | 111@xxx.com |
| 22222222 | B | 222-2222 | 222@xxx.com |
| 33333333 | C | 333-3333 | 333@xxx.com |
| ... | | | |

LOCAL STORE FILE 802

| STORE NO. | STORE NAME | PHONE NO. | E-MAIL ADDRESS | LOCATION | CLASSIFI-CATION |
|---|---|---|---|---|---|
| aaa | A | 444-4444 | a@xxx.com | X CITY | MEDICAL |
| bbb | B | 555-5555 | b@xxx.com | Y CITY | MEDICAL |
| ccc | C | 666-6666 | c@xxx.com | Z CITY | MEDICAL |
| ddd | D | 777-7777 | d@xxx.com | X CITY | VIDEO RENT |
| eee | E | 888-8888 | e@xxx.com | X CITY | MOBIL PHONE |
| ... | | | | | |

TRANSMISSION MESSAGE SELECTION DISPLAY
USER ID: 123     USER NEME: yamada taro
THE FOLLOWING IS YOUR REGISTERED INFORMATION

|   | REGISTERED INFO | REMARKS |
|---|---|---|
| ☑ | INSURENCE CERTIFICATE | NEEDS AUTHORITY CHECK |
| ☐ | DRIVER'S LICENSE | NEEDS AUTHORITY CHECK |
| ☐ | OTHER | SELECTED FROM LIST |

○ ADDRESS
○ PHONE NO
○ E-MAIL ADDRESS
○ BIRTH DATE
○ PHOTO

[ OK ] [ CANCEL ]

902

DESTINATION SELECTION DISPLAY
USER ID: 123     USER NEME: yamada taro
THE FOLLOWING IS YOUR REGISTERED INFORMATION

|   | STORE NAME | LOCATION | CLASSIFICATION |
|---|---|---|---|
| ☐ | A | X CITY | MEDICAL |
| ☐ | B | Y CITY | MEDICAL |
| ☑ | C | Z CITY | MEDICAL |
| ☐ | D | X CITY | VIDEO RENT |
| ☐ | E | X CITY | MOBIL PHONE |

[ OK ] [ CANCEL ]

FIG.10

```
TO: c@xxx.com
SUBJECT: PERSONAL INFORMATION

TO: PERSONNEL IN CHAREGE OF "C"HOSPITAL

NAME:            yamada taro
SYMBOL:          1111
CERTIFICATE NO:  111111
SEX:             male
DATE OF BIRTH:   1967/10/09
INSURANCE NO:    11111111
AUTHORITY:       "A" associate
DATE OF ISSUANCE: 2000/04/01
```
~1001

FIG.11

USER FILE

| USER ID | PASS WORD | USER NAME | ADDRESS | PHONE NO. | E-MAIL ADDRESS | HIC | DL |
|---|---|---|---|---|---|---|---|
| yamada | 123 | yamada taro | K city | 123-4567 | yamada@xxx.com | 1 | 1 |
| sato | 456 | sato hanako | Y city | 890-1234 | sato@xxx.com | 1 | 0 |
| suzuki | 789 | suzuki ken | O city | 567-8901 | suzuki@xxx.com | 0 | 0 |
| ... | | | | | | | |

| SYMBOL | CERTIFICATE NO. | SEX | DATE OF BIRTH | INSURANCE NO. | DATE OF ISSUANCE |
|---|---|---|---|---|---|
| 1111 | 111111 | 1 | 1967/10/09 | 11111111 | 2000/04/01 |
| 2222 | 222222 | 2 | 1967/04/11 | 22222222 | 2000/04/01 |
| ... | | | | | |

101

| LICENSSE NO. | IMAGE INDEX | EXPIRATION DATE |
|---|---|---|
| 111111 | C:¥data¥license¥11111111111.gif | 2001/10/09 |
| — | — | — |
| — | — | — |

FIG.12

ITEM/GROUP FILE 1201

| GROUP | TRANSMISSION ITEMS |
|---|---|
| HIC | USER NAME, ADDRESS, PHONE NO., SYMBOL, CERTIFICATE NO., SEX, BIRTH DATE, ISSUE DATE |
| DL | USER NAME, ADDRESS, PHONE NO., BIRTH DATE, LICENSE NO., IMAGE INDEX, EXPIRATION DATE |

PERSONAL INFORMATION INTERMEDIARY METHOD

BACKGROUND OF THE INVENTION

1. Field of the Invention

The present invention relates to a personal information intermediary method that presents the personal information to a service provider instead of the user when the user desires to receive a service from the service provider, and eliminates the need for the user to carry a driver's license or a health insurance certificate.

2. Description of the Related Art

There is a case in which the user is required to supply the personal information to a service provider when the user desires to receive a certain service. For example, when the user who is the insured in a health insurance association desires to receive a medical treatment, the user must present the health insurance certificate, which describes the insurance certificate identifier, the insurance association identifier or the like, to a hospital or a clinic. When the user desires to obtain a membership card of a rental-video service store, the user has to supply the driver's license to the service store, for the purpose of guaranteeing the user's identification. The photograph of the user himself is usually attached to the driver's license, and it is helpful to authenticate the user at the service store.

However, according to the conventional personal information confirmation method described above, the user must always carry the health insurance certificate or the driver's license when receiving the service such as medical treatment or a video-rental service. If the user fails to carry the health insurance certificate or the driver's license, the user is never allowed to receive the service. It is desirable to provide a personal information intermediary method that easily and safely allows the user to receive the service with no need to always carry it.

SUMMARY OF THE INVENTION

An object of the present invention is to provide an improved personal information intermediary method in which the above-described problems are eliminated.

Another object of the present invention is to provide a personal information intermediary method that allows the user to receive the service by easily and safely presenting the personal information to the service provider instead of the user, and eliminates the need for the user to always carry the health insurance certificate or the driver's license on such an occasion.

The above-mentioned objects of the present invention are achieved by a personal information intermediary method which is performed by an intermediary system having a first recording medium that stores respective items of personal information of registered users and a second recording medium that stores respective items of destination information of registered local terminals, comprising the steps of: receiving a transmission request, including a personal information selection result and a destination selection result, which is sent by a particular user among the registered users; reading a personal information item from the first recording medium, the personal information item corresponding to the personal information selection result of the received transmission request; reading a destination information item from the second recording medium, the destination information item corresponding to the destination selection result of the received transmission request; and transmitting the personal information item of the particular user to a particular local terminal among the registered local terminals that is indicated by the destination information item.

The above-mentioned objects of the present invention are achieved by a computer program which causes a computer to execute a personal information intermediary method, the computer having a first recording medium that stores respective items of personal information of registered users and a second recording medium that stores respective items of destination information of registered local terminals, the computer program comprising: a first program code device which causes the computer to receive a transmission request, including a personal information selection result and a destination selection result, which is sent by a particular user among the registered users; a second program code device which causes the computer to read a personal information item from the first recording medium, the personal information item corresponding to the personal information selection result of the received transmission request; a third program code device which causes the computer to read a destination information item from the second recording medium, the destination information item corresponding to the destination selection result of the received transmission request; and a fourth program code device which causes the computer to transmit the personal information item of the particular user to a particular local terminal among the registered local terminals that is indicated by the destination information item.

The above-mentioned objects of the present invention are achieved by a computer-readable storage medium storing program code instructions causing a computer to execute a personal information intermediary method, the computer having a first recording medium that stores respective items of personal information of registered users and a second recording medium that stores respective items of destination information of registered local terminals, the computer-readable storage medium comprising: a first program code device which causes the computer to receive a transmission request, including a personal information selection result and a destination selection result, which is sent by a particular user among the registered users; a second program code device which causes the computer to read a personal information item from the first recording medium, the personal information item corresponding to the personal information selection result of the received transmission request; a third program code device which causes the computer to read a destination information item from the second recording medium, the destination information item corresponding to the destination selection result of the received transmission request; and a fourth program code device which causes the computer to transmit the personal information item of the particular user to a particular local terminal among the registered local terminals that is indicated by the destination information item.

The above-mentioned objects of the present invention are achieved by a personal information intermediary system comprising: a first recording medium which stores respective items of personal information of registered users; a second recording medium which stores respective items of destination information of registered local terminals; a receiving unit which receives a transmission request, including a personal information selection result and a destination selection result, which is sent by a particular user among the registered users; a personal information editing unit which reads a personal information item from the first recording medium, the personal information item corresponding to the personal information selection result of the received transmission request, and the personal information editing unit reading a destination information item from the second recording medium, the destination information item corresponding to the destination selection result of the received transmission request; and a personal information transmitting unit which transmits the personal information item of the particular user to a particular local terminal among the registered local terminals that is indicated by the destination information item.

The personal information intermediary method of the present invention is effective in easily and safely presenting the personal information to the service provider instead of the user, so as to allow the user to receive the service from the service provider and to eliminate the need for the user to always carry the health insurance certificate or the driver's license on such an occasion. This will make it possible for the user of a mobile telephone to receive the service from the service provider by simply sending a request to the personal information intermediary site. As the service provider is identified by the destination information registered in the personal information intermediary site, there is no risk of the personal information intermediary method transmitting the personal information of the user to an erroneous destination. It is possible for the present invention to easily and safely supply the personal information to the correct service provider instead of the user.

BRIEF DESCRIPTION OF THE DRAWINGS

Other objects, features and advantages of the present invention will become apparent from the following detailed description when read in conjunction with the accompanying drawings.

FIG. 1 is a diagram of one preferred embodiment of the personal information intermediary system of the present invention.

FIG. 2 is a flowchart for explaining a main routine of the personal information intermediary method executed by the personal information intermediary system of FIG. 1.

FIG. 3 is a flowchart for explaining a user authentication process in the main routine of FIG. 2.

FIG. 4 is a flowchart for explaining a transmission request receiving process in the main routine of FIG. 2.

FIG. 5 is a flowchart for explaining an authority confirmation process in the main routine of FIG. 2.

FIG. 6 is a flowchart for explaining a personal information editing/transmission process in the main routine of FIG. 2.

FIG. 7 is a diagram showing examples of a user file, a health insurance certificate file and a driver license file.

FIG. 8 is a diagram showing examples of an insurance authority file and a local store file.

FIG. 9 is a diagram showing examples of a transmission message selection display and a destination selection display.

FIG. 10 is a diagram showing an example of a personal information message.

FIG. 11 is a diagram showing an example of a user file.

FIG. 12 is a diagram showing an example of an item/group file that defines the relationship between transmission items and groups.

DETAILED DESCRIPTION OF PREFERRED EMBODIMENTS

A description will now be provided of preferred embodiments of the present invention with reference to the accompanying drawings.

FIG. 1 is a diagram of one preferred embodiment of the personal information intermediary system of the present invention.

As shown, the personal information intermediary system 105 of the present embodiment is provided within a personal information intermediary site 101. The personal information intermediary site 101 is, for example, an affiliated corporate body that is established by a plurality of companies and operated by a third party organization that is believed reliable. The personal information intermediary system 105 may be constructed by a computer system.

The personal information intermediary system 105 is provided with a communication control unit. Similarly, a user terminal 102, a local terminal 103 and an authority terminal 104 are provided with respective communication control units. By using the communication control units, a connection between the user terminal 102 and the personal information intermediary system 105 is established via the Internet. The user terminal 102 includes browser software incorporated therein, and the user on the user terminal 102 can communicate with the personal information intermediary system 105 via the Internet during the execution of the software. In the present embodiment, the user terminal 102 may be constructed by a mobile telephone or a personal computer.

Further, by using the communication control units, a connection between the local terminal 103 and the personal information intermediary system 105 is established via the Internet. In the present embodiment, the local terminal 103 may be installed in a certain local store which provides goods or services for the user, or in a hospital which provides medical treatment for the user.

Further, by using the communication control unit, a connection between the authority terminal 104 and the personal information intermediary system 105 is established via the Internet. In the present embodiment, the authority terminal 104 may be installed in a building of a certain authority that is, for example, a health insurance authority which issues the health insurance certificates or a police office which issues the driver's licenses.

As shown in FIG. 1, the personal information intermediary system 105 includes a receiving program 106, a transmission program 107, a transmission message editing program 108, and an authority confirmation program 109. The receiving program 106 is provided to receive information from any of the user terminal 102, the local terminal 103 and the authority terminal 104 via the Internet. The information that is received by the receiving program 106 is called the received information. The transmission program 107 is provided to transmit information to any of the user terminal 102, the local terminal 103 and the authority terminal 104 via the Internet. The information which is transmitted by the transmission program 107 is called the transmission information or message. The transmission message editing program 108 is provided to access some file of the personal information intermediary system 105 based on the received information obtained by the receiving program 106, and to edit the transmission message to be transmitted by the transmission program 107. The authority confirmation program 109 is provided to request the confirmation of the related authority when the transmission message editing program 108 determines that the authority confirmation is needed.

Further, the personal information intermediary system 105 includes an internal storage device and an external storage device. The above programs 106 through 109 are stored in the external storage device. Before the execution of any of the programs 106 through 109 starts, the relevant program is loaded from the external storage device into the internal storage device.

Further, the personal information intermediary system 105 a first recording medium that stores a group of personal information files 110 each containing respective personal information of registered users, a second recording medium that stores a group of destination information files 111 each containing respective destination information of registered local terminals, and a third recording medium that stores a group of authority information files 112 each containing respective authority information of the authorities. When the necessity arises, these files 110-112 are accessed or renewed by any of the receiving program 106, the transmission program 107, the transmission message editing program 108 and the authority confirmation program 109.

FIG. 2 is a flowchart for explaining a main routine of the personal information intermediary method executed by the intermediary system 105 of FIG. 1.

As shown in FIG. 2, at a start of the main routine, the intermediary system 105 at step S201 performs a user authentication process with the user terminal 102. Before the user sends the personal information to the local terminal 103, the connection between the user terminal 102 and the intermediary system 105 is established.

In the intermediary system 105, the personal information of the user as well as the user ID and the password of the user are registered in advance. In the step S201, the user on the user terminal 102 sends the log-in message, including the user ID and the password input by the user, to the intermediary system 105. In response to the log-in message, the intermediary system 105 performs the user authentication process, which will be described later in greater detail.

After the step S201 is performed, the intermediary system 105 at step S202 performs a transmission request receiving process with the user terminal 102. In the step S202, the user terminal 102 sends the personal information selection result and the destination selection result to the intermediary system 105, and the intermediary system 105 receives the user's selection results from the user terminal 102, which will be described later in greater detail.

After the step S202 is performed, the intermediary system at step S203 determines whether the authority confirmation is needed. If the health insurance certificate or the driver's license has to be presented to the local store (or the service provider) in order to receive the service from the local store, it is determined that the authority confirmation is needed. If not, it is determined that the authority confirmation is not needed.

When the result at the step S203 is affirmative, the control of the intermediary system 105 is transferred to step S204. When the result at the step S203 is negative, the control of the intermediary system 105 is transferred to step S205 and the step S204 is not performed.

The intermediary system 105 at step S204 performs an authority confirmation process with the authority terminal 104, which will be described later.

After the step S204 is performed, or when the result at the step S203 is negative, the intermediary system 105 at step S205 performs a personal information editing/transmitting process with the local terminal 103, which will be described later.

Through the execution of the above-described main routine, the user on the user terminal 102 can transmit the personal information (which is the transmission message selected or specified by the user), to the local terminal 103 (the location of which is selected by the user) via the Internet.

Next, FIG. 3 is a flowchart for explaining the user authentication process S201 in the main routine of FIG. 2.

As shown in FIG. 3, at a start of the user authentication process, the user terminal 102 at step S301 transmits the log-in message to the intermediary system 105 via the Internet. The user on the user terminal 102 inputs the user ID and the password, and the user terminal 102 sends the log-in message, including the user ID and the password, to the intermediary system 105.

In response, the intermediary system 105 at step S302 receives the log-in message from the user terminal 102. The intermediary system 105 at step S303 retrieves the personal information files 110 based on the received log-in message.

The personal information files 110 are comprised of a user file 701, a health insurance certificate file 702 and a driver's license file 703. FIG. 7 shows examples of the user file 701, the health insurance certificate file 702 and the driver's license file 703.

As shown in FIG. 7, each record of the user file 701 is comprised of the user ID, the password, the user name, the address, the phone number, the e-mail address, the HIC (health insurance certificate) item, and the DL (driver license) item. These items are used to identify each user. When a corresponding record of the user file 701 includes the HIC item indicating value one ("1"), it means that the user has registered the HIC for that record in the intermediary system 105. The HIC item indicating value zero ("0") means that the user has not registered the HIC for that record. Similarly, when a corresponding record of the user file 701 includes the DL item indicating value one ("1"), it means that the user has registered the DL in the intermediary system 105. The DL item indicating value zero ("0") means that the user has not registered the DL for that record.

As shown in FIG. 7, each record of the health insurance certificate file 702 is comprised of the user ID, the certificate symbol, the certificate number, the sex, the date of birth, the insurance number, and the date of issuance. These items are used to identify each user.

As shown in FIG. 7, each record of the driver license file 703 is comprised of the user ID, the date of birth, the license number, the image index, and the expiration date. These items are used to identify each user.

In the present embodiment, the intermediary system 105 at the step S303 reads the user ID and the password of the corresponding record from the user file 701 by using, as the retrieval key, the user ID of the log-in message received at the step S302.

The intermediary system 105 at step S304 determines whether the user ID and the password, obtained at the step S304, match with the user ID and the password of the received log-in message. When the result at the step S304 is affirmative, the user authentication process of FIG. 3 is successfully complete.

When the result at the step S304 is negative, it is determined that the user authentication process abnormally ends. The intermediary system 105 at step S305 transmits a request of re-transmission of the log-in message to the user terminal 102 via the Internet. At this time, the user on the user terminal 102 is requested to transmit the log-in message to the intermediary system 105 again.

Next, FIG. 4 is a flowchart for explaining the transmission request receiving process S202 in the main routine of FIG. 2.

As shown in FIG. 4, at a start of the transmission request receiving process, the intermediary system 105 at step S401 retrieves the personal information files 110. This retrieving process is a preprocessing needed to create the transmission message selection display at the next step S402. In the step S401, the intermediary system 105 retrieves the registered information of the personal information files 110 by using, as the retrieval key, the user ID of the received log-in message at the step S201.

The intermediary system 105 at step S402 creates the transmission message selection display based on the retrieval result obtained at the step S401. In the step S402, the intermediary system 105 creates the transmission message selection display 901, shown in FIG. 9, based on the retrieval results from the user file 701, the health insurance certificate file 702 and the driver's license file 703 which are included in the personal information files 110.

As shown in FIG. 9, the transmission message selection display 901 is divided into a header, a body portion and a footer. In the header of the transmission message selection display 901, the user ID and the user name are described. The user ID of the received log-in message is transferred to the corresponding location of the header. The user name of the corresponding record of the retrieval results obtained at the step S401 is transferred to the corresponding location of the header.

In the body portion of the transmission message selection display 901, several registered items are described. When the corresponding record of the user file 701 (which matches with the user ID and the user name of the log-in message) includes the HIC item indicating the value one ("1"), the health insurance certificate (HIC) line is included in the body portion of the transmission message selection display 901 as the registered item. As previously described, the HIC item of the user file 701, which indicates the value one, means that the user has registered the HIC item in the intermediary system 105.

When the corresponding record of the user file 701 includes the DL item indicating the value one ("1"), the driver's license (DL) line is included in the body portion of the selection display 901 as the registered item. As previously described, the DL item of the user file 701, which indicates the value one, means that the user has registered the DL item in the intermediary system 105. On the other hand, when the corresponding record of the user file 701 includes the HIC item and the DL item, which indicate the value zero ("0"), the body portion of the selection display 901 includes neither the HIC line nor the DL line as the registered item.

Further, the other item line is always included in the body portion of the selection display 901. A set of check boxes of the other items (the address, the phone number, the e-mail address, the date of birth, and the photograph), which are freely selected by the user, is provided adjacent to the other item line in the body portion of the selection display 901 as shown in FIG. 9.

In the footer of the selection display 901, the "OK" button and the "CANCEL" button are provided. When the "OK" button is clicked after the personal information selection is performed by the user, the personal information selection result is transmitted from the user terminal 102 to the intermediary system 105 via the Internet. When the "CANCEL" button is clicked, the process is terminated without the transmission.

After the step S402 is performed, the intermediary system 105 at step S403 transmits the personal information selection display (or the selection display 901) to the user terminal 102 via the Internet.

In response, the user terminal 102 at step S404 receives the personal information selection display from the intermediary system 105. In the user terminal 102, the received personal information selection display appears on the display device (not shown). The user on the user terminal 102 selects the personal information items, which are sent to the local terminal 103, while viewing the selection display. Specifically, the user selects the personal information items in the body portion of the transmission message selection display 901.

The user terminal 102 at step S405 transmits the personal information selection result to the intermediary system 105 via the Internet when the "OK" button in the footer of the selection display 901 is clicked by the user.

The intermediary system 105 at step S406 receives the personal information result from the user terminal 102.

Next, the intermediary system 105 at step S407 retrieves the destination information files 111. This retrieving process is a preprocessing needed to create the destination selection display at the next step S408.

The intermediary system 105 at step S408 creates the destination selection display based on the retrieval result obtained at the step S407. In the step S408, the intermediary system 105 creates the destination selection display 902, shown in FIG. 9, based on the retrieval results from the local store file 802 which is included in the destination information files 111.

As shown in FIG. 8, each record of the local store file 802 is comprised of the store number, the store name, the phone number, the e-mail address, the location and the classification. Among these items, the store name, the location and the classification of the respective records of the local store file 802 are transferred to the corresponding items of the destination selection display 902.

As shown in FIG. 9, the destination selection display 902 is divided into a header, a body portion and a footer. In the header of the destination selection display 902, the user ID and the user name are described. The user ID of the received log-in message is transferred to the corresponding location of the header. The user name of the corresponding record of the retrieval results obtained at the step S401 is transferred to the corresponding location of the header.

In the body portion of the destination selection display 902, several registered items are described. The lines corresponding to all the records of the local store file 802 are included in the body portion of the destination selection display 902. Each line of the body portion of the destination selection display 902 includes the store name, the location and the classification. A set of check boxes of these items which are freely selected by the user, is provided in the body portion of the selection display 902 as shown in FIG. 9.

In the footer of the selection display 902, the "OK" button and the "CANCEL" button are provided. When the "OK" button is clicked after the destination selection is performed by the user, the destination selection result is transmitted from the user terminal 102 to the intermediary system 105 via the Internet. When the "CANCEL" button is clicked, the process is terminated without the transmission.

After the step S408 is performed, the intermediary system 105 at step S409 transmits the destination selection display (or the selection display 902) to the user terminal 102 via the Internet.

In response, the user terminal 102 at step S410 receives the destination selection display from the intermediary system 105. In the user terminal 102, the received destination selection display appears on the display device of the user terminal 102. The user on the user terminal 102 selects the destination to which the personal information is sent while viewing the selection display 902. Specifically, the user selects the items in the body portion of the destination selection display 902.

The user terminal 102 at step S411 transmits the destination selection result to the intermediary system 105 via the Internet when the "OK" button in the footer of the selection display 902 is clicked by the user.

In response, the intermediary system 105 at step S412 receives the destination selection result from the user terminal 102. After the step S412 is performed, the transmission request receiving process of FIG. 4 ends.

In the above-described transmission request receiving process, the receiving of the personal information selection result and the receiving of the destination selection result are separately performed in this order. However, the present invention is not limited to this embodiment. Alternatively, the receiving of the personal information selection result and the receiving of the destination selection result may be performed simultaneously. Further, it is possible to perform the receiving of the destination selection result first and the receiving of the personal information selection result second in the reverse order.

Next, FIG. 5 is a flowchart for explaining the authority confirmation process S204 in the main routine of FIG. 2.

The authority confirmation process shown in FIG. 5 is executed when it is determined at the step S203 that the confirmation of the authority is needed. For example, the personnel on the authority terminal 104 of the insurance authority or the police office confirms the authenticity of the personal information presented by the personal information intermediary system.

As shown in FIG. 5, at a start of the authority confirmation process, the intermediary system 105 at step S501 retrieves the authority information files 112 based on the selected destination of the transmission request received at step S202.

In the step S501, the body portion of the transmission message selection display 901, which is received from the user terminal 102, is read by the intermediary system 105. Suppose that the body portion of the received transmission selection display 901, in the present embodiment, contains the health insurance certificate (HIC) item selected by the user. In this case, the health insurance certificate file 702 is retrieved by using the user ID as the retrieval key.

On the other hand, when the body portion of the received transmission selection display 901 contains the driver's license (DL) item selected by the user, the driver's license file 703 is retrieved by using the user ID as the retrieval key in the step S501.

The intermediary system 105 at step S502 creates the confirmation request message that is sent from the intermediary system 105 to the authority terminal 104 via the Internet.

In the step S502, the confirmation request message is created based on the contents of the personal information files 110. The confirmation request message contains the items needed for the confirmation, and is derived from the user file 701, the health insurance certificate file 702 and the driver's license file 703. The destination of the confirmation request message depends on the selected item (HIC or DL) of the transmission message. When the HIC item is selected in the transmission message, the insurance authority file 801 (FIG. 8) among the authority information files 112 is retrieved in the step S502. Each record of the insurance authority file 801 shown in FIG. 8 contains the insurance number, the insurance authority (I/A) name, the phone number and the e-mail address. The confirmation request message is sent from the intermediary system 105 to the authority terminal 104 based on the e-mail address of the corresponding record of the insurance authority file 801.

On the other hand, when the DL item is selected in the transmission message, the confirmation request message is sent from the intermediary system 105 to the authority terminal 104 of the police office. The destination of request message in this case is a fixed destination. There is no need to prepare a special file.

The intermediary system 105 at step S503 sends the confirmation request message, which is created at the step S502, to the authority terminal 104 via the Internet.

In response, the authority terminal 104 at step S504 receives the confirmation request message from the intermediary system 105 via the Internet. At this time, the personnel on the authority terminal 104 confirms the authenticity of the personal information presented by the intermediary system 105. The authority terminal 104 at step S505 sends the confirmation result message to the intermediary system 105 via the Internet.

The intermediary system 105 at step S506 receives the confirmation result message from the authority terminal 104 via the Internet. Based on the received confirmation result message, the intermediary system 105 at step S507 determines whether the presented personal information is valid. When the result at the step S507 is affirmative, the authority confirmation process of FIG. 5 is successfully complete, and the user is allowed to receive the desired service from the service provider. Otherwise, the intermediary system 105 at step S508 sends a notice of invalid information to the user terminal 102 via the Internet. In the latter case, the user is not allowed to receive the desired service from the service provider.

Next, FIG. 6 is a flowchart for explaining the personal information editing/transmitting process S205 in the main routine of FIG. 2.

As shown in FIG. 6, at a start of the personal information editing/transmitting process, the intermediary system 105 at step S601 performs the personal information editing process. In the foregoing processes, the personal information selection result and the destination selection result, which are sent from the user terminal 102, have been received at the intermediary system 105. In the step S601, the intermediary system 105 creates the personal information message, which is sent to the local terminal 103, based on these selection results.

FIG. 10 shows an example of the personal information message that is created in the step S601 in FIG. 6. In the present embodiment, the personal information message 1001, which is created by the intermediary system 105, is transmitted to the local terminal 103 as the e-mail. Alternatively, the personal information message 1001 may be sent to the local terminal 103 as the facsimile or the mail.

As shown in FIG. 10, the e-mail address is described at the beginning of the personal information message 1001. The corresponding e-mail address of the "C" hospital record, read from the local store file 802, is transferred to this e-mail address at the first line of the message 1001. The subject "personal information" at the second line of the message 1001 is a fixed message. The subsequent items of the personal information message 1001 are derived from the user file 701, the health insurance certificate file 702, the insurance authority file 801, and the local storage file 802.

After the personal information message 1001 is created, the intermediary system 105 at step S602 transmits the personal information message (as shown in FIG. 10) to the local terminal 103 via the Internet.

In the above-described embodiment, the personal information files 110 are comprised of the user file 701, the health insurance certificate file 702, and the driver's license file 703. Alternatively, the personal information files 110 may be constructed by a different user file and an item/group file, which will now be described in the following.

FIG. 11 shows an example of a user file 1101 that is used in the alternative embodiment. As shown, the registered personal information items included in the user file 1101 are similar to the corresponding items in the previous embodiment of FIG. 7 but the duplicate items in the previous embodiment are omitted. The user file 1101 employs a simplified file layout, and it is possible to have an access to the user file 1101 more efficiently.

However, one record of the user file 1101 contains both the health insurance certificate (HIC) information items and the driver's license (DL) information items. When sending the health insurance certificate (HIC) information, or when sending the driver's license (DL) information, it is difficult to determine which items should be included in the transmission message. To eliminate the problem, an item/group file for use with the user file 1101 of the alternative embodiment is needed. The item/group file is provided to define the relationship between transmission items and groups.

FIG. 12 shows an example of the item/group file 1201 that defines the relationship between transmission items and groups. As shown, each record of the item/group file 1201 include a group and transmission items. For example, suppose that the health insurance certificate (HIC) is selected in the transmission message selection display 901. In this case, the item/group file 1201 is retrieved, and the record including the HIC group is read from the item/group 1201. It can be determined from the contents of this record that the transmission items are the user name, the address, the phone number, the certificate symbol, the certificate number, the sex, the date of birth, and the date of issuance.

The programs that execute the personal information intermediary method to achieve the objects of the present invention may be provided by the transmission of the programs through the network. Further, the programs may be provided in the form of a computer-readable storage medium, such as a floppy disk, which stores the program code instructions causing the computer to execute the personal information intermediary method to achieve the objects of the present invention.

The present invention is not limited to the above-described embodiments, and variations and modifications may be made without departing from the scope of the present invention.

Further, the present invention is based on Japanese priority application No. 2001-170455, filed on Jun. 6, 2001, the entire contents of which are hereby incorporated by reference.

What is claimed is:

1. A personal information intermediary method which is performed by an intermediary system having a first recording medium that stores respective items of personal information of registered users and a second recording medium that stores respective items of destination information of registered local terminals, comprising:

receiving a transmission request, including a personal information selection result and a destination selection result, which is sent by a particular user among the registered users, wherein the intermediary system has an item/group file defining a relationship between transmission items and predefined groups of the personal information, and wherein the personal information selection result indicates a result of the particular user's selection of a group, from among the predefined groups, of the particular user's personal information, wherein each group of the particular user's personal information may comprise one or plural items of personal information within the respective group;

acquiring a requested personal information item from the first recording medium by retrieving the item/group file to obtain correspondence between the requested personal information item and the selected personal information group indicated by the personal information selection result;

acquiring a requested destination information item from the second recording medium, the requested destination information item corresponding to the destination selection result of the received transmission request;

transmitting the personal information item of the particular user to a particular local terminal among the registered local terminals that is indicated by the destination information item; and receiving a confirmation result message from an authority terminal, the confirmation result message confirming the authenticity of the transmitted personal information, wherein when an authority confirmation is needed for the received transmission request and the requested personal information item is either a health insurance certificate item or a driver's license item, a confirmation request message is created by retrieving the item/group file and reading from the item/group file a record corresponding to either the health insurance certificate item or the driver's license item, and the confirmation request message is transmitted to the authority terminal.

2. The personal information intermediary method according to claim 1, further comprising transmitting, prior to said receiving a transmission request, a destination selection display to the particular user to select the destination information item, the destination selection display including a list of the respective destination information items of the registered local terminals.

3. A computer readable storage medium storing a program which causes a computer, having a first recording medium that stores respective items of personal information of registered users and a second recording medium that stores respective items of destination information of registered local terminals, to execute a personal information intermediary method comprising:

first program code means for causing the computer to receive a transmission request, including a personal information selection result and a destination selection result, which is sent by a particular user among the registered users, wherein an item/group file defines a relationship between transmission items and predefined groups of the personal information, and wherein the personal information selection result indicates a result of the particular user's selection of a group, from among the predefined groups, of the particular user's personal information, wherein each group of the particular user's personal information may comprise one or plural items of personal information within the respective group;

second program code means for causing the computer to acquire a requested personal information item from the first recording medium by retrieving the item/group file to obtain correspondence between the requested personal information item and the selected personal information group indicated by the personal information selection result;

third program code means for causing the computer to acquire a requested destination information item from the second recording medium, the requested destination information item corresponding to the destination selection result of the received transmission request;

fourth program code means for causing the computer to transmit the personal information item of the particular user to a particular local terminal among the registered local terminals that is indicated by the destination information item; and fifth program code means for causing the computer to receive a confirmation result message from an authority terminal, the confirmation result message confirming the authenticity of the transmitted personal information, wherein when an authority confirmation is needed for the received transmission request and the requested personal information item is either a health insurance certificate item or a driver's license item, a confirmation request message is created by retrieving the item/group file and reading from the item/group file a record corresponding to either the health insurance certificate item or the driver's license item, and the confirmation request message is transmitted to the authority terminal.

4. A computer-readable storage medium storing program code instructions causing a computer, having a first recording medium that stores respective items of personal information of registered users and a second recording medium that stores respective items of destination information of registered local terminals, to execute a personal information intermediary method, comprising:

causing the computer to receive a transmission request, including a personal information selection result and a destination selection result, which is sent by a particular user among the registered users, wherein an item/group file defines a relationship between transmission items and predefined groups of the personal information, and wherein the personal information selection result indicates a result of the particular user's selection of a group, from among the predefined groups, of the particular user's personal information, wherein each group of the particular user's personal information may comprise one or plural items of personal information within the respective group;

causing the computer to acquire a requested personal information item from the first recording medium by retrieving the item/group file to obtain correspondence between the requested personal information item and the selected personal information group indicated by the personal information selection result;

causing the computer to acquire a requested destination information item from the second recording medium, the requested destination information item corresponding to the destination selection result of the received transmission request;

causing the computer to transmit the personal information item of the particular user to a particular local terminal among the registered local terminals that is indicated by the destination information item; and causing the computer to receive a confirmation result message from an authority terminal, the confirmation result message confirming the authenticity of the transmitted personal information, wherein when an authority confirmation is needed for the received transmission request and the requested personal information item is either a health insurance certificate item or a driver's license item, a confirmation request message is created by retrieving the item/group file and reading from the item/group file a record corresponding to either the health insurance certificate item or the driver's license item, and the confirmation request message is transmitted to the authority terminal.

5. A personal information intermediary computer system comprising:

a first recording medium storing respective items of personal information of registered users;

a second recording medium storing respective items of destination information of registered local terminals; and a programmed computer processor controlling the system according to a process comprising:

receiving a transmission request, including a personal information selection result and a destination selection result, which is sent by a particular user among the registered users, wherein an item/group file defines a relationship between transmission items and predefined groups of the personal information, and wherein the personal information selection result indicates a result of the particular user's selection of a group, from among the predefined groups, of the particular user's personal information, wherein each group of the particular user's personal information may comprise one or plural items of personal information within the respective group;

acquiring a requested personal information item from the first recording medium by retrieving the item/group file to obtain correspondence between the requested personal information item and the selected personal information group indicated by the personal information selection;

acquiring a requested destination information item from the second recording medium, the destination information item corresponding to the requested destination selection result of the received transmission request;

transmitting the personal information item of the particular user to a particular local terminal among the registered local terminals indicated by the destination information item; and receiving a confirmation result message from an authority terminal, the confirmation result message confirming the authenticity of the transmitted personal information, wherein when an authority confirmation is needed for the received transmission request and the requested personal information item is either a health insurance certificate item or a driver's license item, a confirmation request message is created by retrieving the item/group file and reading from the item/group file a record corresponding to either the health insurance certificate item or the driver's license item, and the confirmation request message is transmitted to the authority terminal.

* * * * *